US010166033B2

(12) United States Patent
Reiley et al.

(10) Patent No.: US 10,166,033 B2
(45) Date of Patent: Jan. 1, 2019

(54) IMPLANTS FOR BONE FIXATION OR FUSION

(71) Applicant: SI-Bone Inc., San Jose, CA (US)

(72) Inventors: Mark A. Reiley, Washington, DC (US); Bret W. Schneider, Morgan Hill, CA (US); Joanne Leung, Mountain View, CA (US); Paul Sand, Redwood City, CA (US); Scott A. Yerby, Montara, CA (US)

(73) Assignee: SI-Bone Inc., Santa Clara, CA (US)

( * ) Notice: Subject to any disclaimer, the term of this patent is extended or adjusted under 35 U.S.C. 154(b) by 305 days.

(21) Appl. No.: 14/859,046

(22) Filed: Sep. 18, 2015

(65) Prior Publication Data

US 2016/0081810 A1 Mar. 24, 2016

Related U.S. Application Data

(60) Provisional application No. 62/052,318, filed on Sep. 18, 2014.

(51) Int. Cl.
*A61F 2/30* (2006.01)
*A61B 17/16* (2006.01)
*A61B 17/17* (2006.01)
*A61F 2/44* (2006.01)
*A61B 17/84* (2006.01)

(52) U.S. Cl.
CPC ...... *A61B 17/1757* (2013.01); *A61B 17/1604* (2013.01); *A61B 17/84* (2013.01); *A61F 2002/30995* (2013.01)

(58) Field of Classification Search
CPC .......... A61F 2/30; A61F 2/30988; A61F 2/44; A61F 2/447; A61F 2/446; A61B 17/16; A61B 17/1642; A61B 17/1615; A61B 17/1631; A61B 17/1671; A61B 17/1757
See application file for complete search history.

(56) References Cited

U.S. PATENT DOCUMENTS

| | | | |
|---|---|---|---|
| 1,951,278 | A | 3/1934 | Ericsson |
| 2,136,471 | A | 11/1938 | Schneider |
| 2,243,717 | A | 5/1941 | Moreira |
| 2,414,882 | A | 7/1947 | Longfellow |

(Continued)

FOREIGN PATENT DOCUMENTS

| | | |
|---|---|---|
| CN | 1128944 A | 8/1996 |
| CN | 1190882 A | 8/1998 |

(Continued)

OTHER PUBLICATIONS

Reiley, Mark A.; U.S. Appl. No. 12/357,483 entitled "Systems and methods for the fixation or fusion of bone in the hand and wrist," filed Jan. 22, 2009 (abandoned).

(Continued)

*Primary Examiner* — Christopher Beccia
(74) *Attorney, Agent, or Firm* — Shay Glenn LLP

(57) ABSTRACT

Implants for the fusion or fixation of two bone segments are described. For example, the implants can be used for the fusion or fixation of the sacroiliac joint. The implants can include fenestrations, have a rectilinear overall cross-sectional area, and have a curvature. Some implants can also be used to rescue failed implants.

8 Claims, 11 Drawing Sheets

(Posterior)

(56) References Cited

U.S. PATENT DOCUMENTS

| | | | |
|---|---|---|---|
| 2,562,419 | A | 7/1951 | Ferris |
| 2,675,801 | A | 4/1954 | Bambara et al. |
| 2,697,433 | A | 12/1954 | Zehnder |
| 3,076,453 | A | 2/1963 | Tronzo |
| 3,506,982 | A | 4/1970 | Steffee |
| 3,694,821 | A | 10/1972 | Moritz |
| 3,709,218 | A | 1/1973 | Halloran |
| 3,744,488 | A | 7/1973 | Cox |
| 4,059,115 | A | 11/1977 | Jumashev et al. |
| 4,156,943 | A | 6/1979 | Collier |
| 4,292,964 | A | 10/1981 | Ulrich |
| 4,341,206 | A | 7/1982 | Perrett et al. |
| 4,344,190 | A | 8/1982 | Lee et al. |
| 4,399,813 | A | 8/1983 | Barber |
| 4,423,721 | A | 1/1984 | Otte et al. |
| 4,475,545 | A | 10/1984 | Ender |
| 4,501,269 | A | 2/1985 | Bagby |
| 4,569,338 | A | 2/1986 | Edwards |
| 4,612,918 | A | 9/1986 | Slocum |
| 4,622,959 | A | 11/1986 | Marcus |
| 4,630,601 | A | 12/1986 | Harder et al. |
| 4,638,799 | A | 1/1987 | Moore |
| 4,657,550 | A | 4/1987 | Daher |
| 4,743,256 | A | 5/1988 | Brantigan |
| 4,773,402 | A | 9/1988 | Asher et al. |
| 4,787,378 | A | 11/1988 | Sodhi |
| 4,790,303 | A | 12/1988 | Steffee |
| 4,834,757 | A | 5/1989 | Brantigan |
| 4,846,162 | A | 7/1989 | Moehring |
| 4,877,019 | A | 10/1989 | Vives |
| 4,878,915 | A | 11/1989 | Brantigan |
| 4,898,186 | A | 2/1990 | Ikada et al. |
| 4,904,261 | A | 2/1990 | Dove et al. |
| 4,950,270 | A | 8/1990 | Bowman et al. |
| 4,961,740 | A | 10/1990 | Ray et al. |
| 4,969,888 | A | 11/1990 | Scholten et al. |
| 4,981,481 | A | 1/1991 | Kranz et al. |
| 5,034,011 | A | 7/1991 | Howland |
| 5,034,013 | A | 7/1991 | Kyle et al. |
| 5,035,697 | A | 7/1991 | Frigg |
| 5,041,118 | A | 8/1991 | Wasilewski |
| 5,053,035 | A | 10/1991 | McLaren |
| 5,059,193 | A | 10/1991 | Kuslich |
| 5,066,296 | A | 11/1991 | Chapman et al. |
| 5,102,414 | A | 4/1992 | Kirsch |
| 5,108,397 | A | 4/1992 | White |
| 5,122,141 | A | 6/1992 | Simpson et al. |
| 5,139,498 | A | 8/1992 | Astudillo Ley |
| 5,139,500 | A | 8/1992 | Schwartz |
| 5,147,367 | A | 9/1992 | Ellis |
| 5,147,402 | A | 9/1992 | Bohler et al. |
| 5,190,551 | A | 3/1993 | Chin |
| 5,197,961 | A | 3/1993 | Castle |
| 5,242,444 | A | 9/1993 | MacMillan |
| 5,298,254 | A | 3/1994 | Prewett et al. |
| 5,334,205 | A | 8/1994 | Cain |
| 5,380,325 | A | 1/1995 | Lahille et al. |
| 5,390,683 | A | 2/1995 | Pisharodi |
| 5,433,718 | A | 7/1995 | Brinker |
| 5,443,466 | A | 8/1995 | Shah |
| 5,458,638 | A | 10/1995 | Kuslich et al. |
| 5,470,334 | A | 11/1995 | Ross et al. |
| 5,480,402 | A | 1/1996 | Kim |
| 5,569,249 | A | 10/1996 | James et al. |
| 5,591,235 | A | 1/1997 | Kuslich |
| 5,593,409 | A | 1/1997 | Michelson |
| 5,609,635 | A | 3/1997 | Michelson |
| 5,609,636 | A | 3/1997 | Kohrs et al. |
| 5,626,616 | A | 5/1997 | Speece |
| 5,643,264 | A | 7/1997 | Sherman et al. |
| 5,645,599 | A | 7/1997 | Samani |
| 5,658,337 | A | 8/1997 | Kohrs et al. |
| 5,667,510 | A | 9/1997 | Combs |
| 5,669,909 | A | 9/1997 | Zdeblick et al. |
| 5,672,178 | A | 9/1997 | Petersen |
| 5,683,391 | A | 11/1997 | Boyd |
| 5,709,683 | A | 1/1998 | Bagby |
| 5,713,904 | A | 2/1998 | Errico et al. |
| 5,716,358 | A | 2/1998 | Ochoa et al. |
| 5,725,581 | A | 3/1998 | Brånemark |
| 5,743,912 | A | 4/1998 | LaHille et al. |
| 5,759,035 | A | 6/1998 | Ricci |
| 5,766,174 | A | 6/1998 | Perry |
| 5,766,252 | A | 6/1998 | Henry et al. |
| 5,766,261 | A | 6/1998 | Neal et al. |
| 5,788,699 | A | 8/1998 | Bobst et al. |
| 5,800,440 | A | 9/1998 | Stead |
| 5,868,749 | A | 2/1999 | Reed |
| 5,897,556 | A | 4/1999 | Drewry et al. |
| 5,928,239 | A | 7/1999 | Mirza |
| 5,941,885 | A | 8/1999 | Jackson |
| 5,961,522 | A | 10/1999 | Mehdizadeh |
| 5,961,554 | A | 10/1999 | Janson et al. |
| 6,010,507 | A | 1/2000 | Rudloff |
| 6,015,409 | A | 1/2000 | Jackson |
| 6,053,916 | A | 4/2000 | Moore |
| 6,056,749 | A | 5/2000 | Kuslich |
| 6,086,589 | A | 7/2000 | Kuslich et al. |
| 6,096,080 | A | 8/2000 | Nicholson et al. |
| 6,120,504 | A | 9/2000 | Brumback et al. |
| 6,143,031 | A | 11/2000 | Knothe et al. |
| 6,197,062 | B1 | 3/2001 | Fenlin |
| 6,210,442 | B1 | 4/2001 | Wing et al. |
| 6,214,049 | B1 | 4/2001 | Gayer et al. |
| 6,221,074 | B1 | 4/2001 | Cole et al. |
| 6,224,607 | B1 | 5/2001 | Michelson |
| 6,241,732 | B1 | 6/2001 | Overaker et al. |
| 6,264,657 | B1 | 7/2001 | Urbahns et al. |
| 6,270,528 | B1 | 8/2001 | McKay |
| 6,287,343 | B1 | 9/2001 | Kuslich et al. |
| 6,302,885 | B1 | 10/2001 | Essiger |
| 6,302,914 | B1 | 10/2001 | Michelson |
| 6,306,140 | B1 | 10/2001 | Siddiqui |
| 6,319,253 | B1 | 11/2001 | Ackeret et al. |
| 6,406,498 | B1 | 6/2002 | Tormala et al. |
| 6,409,768 | B1 | 6/2002 | Tepic et al. |
| 6,451,020 | B1 | 9/2002 | Zucherman et al. |
| 6,471,707 | B1 | 10/2002 | Miller et al. |
| 6,485,518 | B1 | 11/2002 | Cornwall et al. |
| 6,497,707 | B1 | 12/2002 | Bowman et al. |
| 6,517,541 | B1 | 2/2003 | Sesic |
| 6,520,969 | B2 | 2/2003 | Lambrecht et al. |
| 6,524,314 | B1 | 2/2003 | Dean et al. |
| 6,527,775 | B1 | 3/2003 | Warburton |
| 6,558,386 | B1 | 5/2003 | Cragg |
| 6,565,566 | B1 | 5/2003 | Wagner |
| 6,575,899 | B1 | 6/2003 | Foley et al. |
| 6,575,991 | B1 | 6/2003 | Chesbrough et al. |
| 6,579,293 | B1 | 6/2003 | Chandran |
| 6,582,431 | B1 | 6/2003 | Ray |
| 6,595,998 | B2 | 7/2003 | Johnson et al. |
| 6,602,293 | B1 | 8/2003 | Biermann et al. |
| 6,605,090 | B1 | 8/2003 | Trieu et al. |
| 6,607,530 | B1 | 8/2003 | Carl et al. |
| 6,620,163 | B1 | 9/2003 | Michelson |
| 6,635,059 | B2 | 10/2003 | Randall et al. |
| 6,666,868 | B2 | 12/2003 | Fallin |
| 6,669,529 | B1 | 12/2003 | Scaries |
| 6,673,075 | B2 | 1/2004 | Santilli |
| 6,692,501 | B2 | 2/2004 | Michelson |
| 6,723,099 | B1 | 4/2004 | Goshert |
| 6,740,118 | B2 | 5/2004 | Eisermann et al. |
| 6,743,257 | B2 | 6/2004 | Castro |
| D493,533 | S | 7/2004 | Blain |
| 6,793,656 | B1 | 9/2004 | Mathews |
| 6,827,740 | B1 | 12/2004 | Michelson |
| 6,984,235 | B2 | 1/2006 | Huebner |
| 6,991,461 | B2 | 1/2006 | Gittleman |
| 7,118,579 | B2 | 10/2006 | Michelson |
| 7,175,663 | B1 | 2/2007 | Stone |
| 7,211,085 | B2 | 5/2007 | Michelson |
| 7,223,269 | B2 | 5/2007 | Chappuis |
| 7,314,488 | B2 | 1/2008 | Reiley |
| 7,335,205 | B2 | 2/2008 | Aeschlimann et al. |

(56) References Cited

U.S. PATENT DOCUMENTS

| | | |
|---|---|---|
| 7,338,500 B2 | 3/2008 | Chappuis |
| 7,452,359 B1 | 11/2008 | Michelson |
| 7,452,369 B2 | 11/2008 | Barry |
| 7,481,831 B2 | 1/2009 | Bonutti |
| 7,527,649 B1 | 5/2009 | Blain |
| 7,534,254 B1 | 5/2009 | Michelson |
| 7,537,616 B1 | 5/2009 | Branch et al. |
| 7,569,054 B2 | 8/2009 | Michelson |
| 7,569,059 B2 | 8/2009 | Cerundolo |
| 7,601,155 B2 | 10/2009 | Petersen |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,837,735 B2 | 11/2010 | Malone |
| 7,850,732 B2 | 12/2010 | Heinz |
| 7,857,832 B2 | 12/2010 | Culbert et al. |
| 7,887,565 B2 | 2/2011 | Michelson |
| 7,901,439 B2 | 3/2011 | Horton |
| 7,909,832 B2 | 3/2011 | Michelson |
| 7,922,765 B2 | 4/2011 | Reiley |
| 7,942,879 B2 | 5/2011 | Christie et al. |
| 8,052,728 B2 | 11/2011 | Hestad |
| 8,062,365 B2 | 11/2011 | Schwab |
| 8,066,705 B2 | 11/2011 | Michelson |
| 8,066,709 B2 | 11/2011 | Michelson |
| 8,080,046 B2 | 12/2011 | Suddaby |
| 8,142,481 B2 | 3/2012 | Warnick |
| 8,142,503 B2 | 3/2012 | Malone |
| 8,162,981 B2 | 4/2012 | Vestgaarden |
| 8,202,305 B2 | 6/2012 | Reiley |
| 8,308,779 B2 | 11/2012 | Reiley |
| 8,317,862 B2 | 11/2012 | Troger et al. |
| 8,348,950 B2 | 1/2013 | Assell et al. |
| 8,388,667 B2 | 3/2013 | Reiley et al. |
| 8,394,129 B2 | 3/2013 | Morgenstern Lopez |
| 8,398,635 B2 | 3/2013 | Vaidya |
| 8,414,648 B2 | 4/2013 | Reiley |
| 8,425,570 B2 | 4/2013 | Reiley |
| 8,430,930 B2 | 4/2013 | Hunt |
| 8,439,925 B2 | 5/2013 | Marino et al. |
| 8,444,693 B2 | 5/2013 | Reiley |
| 8,470,004 B2 | 6/2013 | Reiley |
| 8,529,608 B2 | 9/2013 | Terrill et al. |
| 8,608,802 B2 | 12/2013 | Bagga et al. |
| D697,209 S | 1/2014 | Walthall et al. |
| 8,641,737 B2 | 2/2014 | Matthis et al. |
| 8,672,986 B2 | 3/2014 | Klaue et al. |
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,858,601 B2 | 10/2014 | Reiley |
| 8,920,477 B2 | 12/2014 | Reiley |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 8,961,571 B2 | 2/2015 | Lee et al. |
| 8,986,348 B2 | 3/2015 | Reiley |
| 9,039,743 B2 | 5/2015 | Reiley |
| 9,044,321 B2 | 6/2015 | Mauldin et al. |
| 9,060,876 B1 | 6/2015 | To et al. |
| 9,089,371 B1 | 7/2015 | Faulhaber |
| D738,498 S | 9/2015 | Frey et al. |
| 9,131,955 B2 | 9/2015 | Swofford |
| 9,149,286 B1 | 10/2015 | Greenhalgh et al. |
| 9,198,676 B2 | 12/2015 | Pilgeram et al. |
| 9,220,535 B2 | 12/2015 | Röbling et al. |
| 9,314,348 B2 | 4/2016 | Emstad |
| 9,358,057 B1 | 6/2016 | Whipple et al. |
| 9,375,243 B1 | 6/2016 | Vestgaarden |
| 9,452,065 B1 | 9/2016 | Lawson |
| 9,492,284 B2 | 11/2016 | Ginn et al. |
| 9,498,264 B2 | 11/2016 | Harshman et al. |
| 9,510,872 B2 | 12/2016 | Donner et al. |
| 9,517,095 B2 | 12/2016 | Vaidya |
| 9,522,028 B2 | 12/2016 | Warren et al. |
| 9,526,548 B2 | 12/2016 | Asfora |
| 9,554,909 B2 | 1/2017 | Donner |
| 9,566,095 B2 | 2/2017 | Lorio |
| 9,566,100 B2 | 2/2017 | Asfora |
| 9,592,131 B2 | 3/2017 | Sandstrom et al. |
| 9,603,613 B2 | 3/2017 | Schoenefeld et al. |
| 9,615,856 B2 | 4/2017 | Arnett et al. |
| 9,636,226 B2 | 5/2017 | Hunt |
| 9,662,124 B2 | 5/2017 | Assell et al. |
| 9,757,154 B2 | 9/2017 | Donner et al. |
| 9,763,695 B2 | 9/2017 | Mirda |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0038123 A1 | 3/2002 | Visotsky et al. |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0128652 A1 | 9/2002 | Ferree |
| 2002/0143334 A1 | 10/2002 | von Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0097131 A1 | 5/2003 | Schon et al. |
| 2003/0139815 A1* | 7/2003 | Grooms ............... A61F 2/4644 623/17.11 |
| 2003/0181979 A1 | 9/2003 | Ferree |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0049590 A1 | 3/2005 | Alleyne et al. |
| 2005/0055023 A1 | 3/2005 | Sohngen et al. |
| 2005/0075641 A1 | 4/2005 | Singhatat et al. |

(56) References Cited

U.S. PATENT DOCUMENTS

| | | |
|---|---|---|
| 2005/0080415 A1 | 4/2005 | Keyer et al. |
| 2005/0107878 A1 | 5/2005 | Conchy |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1 | 7/2005 | Zucherman et al. |
| 2005/0159749 A1 | 7/2005 | Levy et al. |
| 2005/0165398 A1 | 7/2005 | Reiley |
| 2005/0192572 A1 | 9/2005 | Abdelgany et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2005/0277940 A1 | 12/2005 | Neff |
| 2006/0036247 A1 | 2/2006 | Michelson |
| 2006/0036251 A1 | 2/2006 | Reiley |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089656 A1 | 4/2006 | Allard et al. |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1* | 8/2006 | McGraw ............... A61B 17/70 606/279 |
| 2006/0217717 A1 | 9/2006 | Whipple |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161989 A1 | 7/2007 | Heinz et al. |
| 2007/0219634 A1 | 9/2007 | Greenhalgh et al. |
| 2007/0233146 A1 | 10/2007 | Henniges et al. |
| 2007/0250166 A1 | 10/2007 | McKay |
| 2007/0265621 A1 | 11/2007 | Matthis et al. |
| 2007/0270879 A1 | 11/2007 | Isaza et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0109083 A1 | 5/2008 | Van Hoeck et al. |
| 2008/0140082 A1 | 6/2008 | Erdem et al. |
| 2008/0147079 A1 | 6/2008 | Chin et al. |
| 2008/0154374 A1 | 6/2008 | Labrom |
| 2008/0161810 A1 | 7/2008 | Melkent |
| 2008/0183204 A1 | 7/2008 | Greenhalgh et al. |
| 2008/0234758 A1 | 9/2008 | Fisher et al. |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0043393 A1 | 2/2009 | Duggal et al. |
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevoets et al. |
| 2009/0118771 A1* | 5/2009 | Gonzalez-Hernandez ................... A61B 17/1728 606/286 |
| 2009/0131986 A1 | 5/2009 | Lee et al. |
| 2009/0138053 A1 | 5/2009 | Assell |
| 2009/0157119 A1 | 6/2009 | Hale |
| 2009/0163920 A1 | 6/2009 | Hochschuler et al. |
| 2009/0187247 A1 | 7/2009 | Metcalf, Jr. et al. |
| 2009/0216238 A1 | 8/2009 | Stark |
| 2009/0259261 A1 | 10/2009 | Reiley |
| 2009/0270929 A1 | 10/2009 | Suddaby |
| 2009/0287254 A1 | 11/2009 | Nayet et al. |
| 2009/0312798 A1 | 12/2009 | Varela |
| 2009/0324678 A1 | 12/2009 | Thorne et al. |
| 2010/0016903 A1* | 1/2010 | Matityahu ............ A61B 17/866 606/301 |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0145461 A1 | 6/2010 | Landry et al. |
| 2010/0160977 A1 | 6/2010 | Gephart et al. |
| 2010/0191292 A1 | 7/2010 | DeMeo et al. |
| 2010/0198267 A1 | 8/2010 | Vaidya |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0331851 A1 | 12/2010 | Huene |
| 2010/0331893 A1 | 12/2010 | Geist et al. |
| 2011/0009869 A1 | 1/2011 | Marino et al. |
| 2011/0022089 A1 | 1/2011 | Assell et al. |
| 2011/0029019 A1 | 2/2011 | Ainsworth et al. |
| 2011/0040362 A1 | 2/2011 | Godara et al. |
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0082551 A1 | 4/2011 | Kraus |
| 2011/0093020 A1 | 4/2011 | Wu |
| 2011/0098747 A1 | 4/2011 | Donner et al. |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0118796 A1 | 5/2011 | Reiley et al. |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184478 A1 | 7/2011 | Reiley |
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0230966 A1 | 9/2011 | Trieu |
| 2011/0238181 A1 | 9/2011 | Trieu |
| 2011/0257755 A1 | 10/2011 | Bellemere et al. |
| 2011/0264229 A1 | 10/2011 | Donner |
| 2011/0295272 A1 | 12/2011 | Assell et al. |
| 2011/0295370 A1 | 12/2011 | Suh et al. |
| 2011/0313532 A1 | 12/2011 | Hunt |
| 2012/0083887 A1 | 4/2012 | Purcell et al. |
| 2012/0095560 A1 | 4/2012 | Donner |
| 2012/0101530 A1 | 4/2012 | Robling et al. |
| 2012/0179256 A1 | 7/2012 | Reiley |
| 2012/0191191 A1 | 7/2012 | Trieu |
| 2012/0197311 A1 | 8/2012 | Kirschman |
| 2012/0253398 A1 | 10/2012 | Metcalf et al. |

(56) References Cited

U.S. PATENT DOCUMENTS

| | | |
|---|---|---|
| 2012/0259372 A1 | 10/2012 | Glazer et al. |
| 2012/0271424 A1 | 10/2012 | Crawford |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0085535 A1 | 4/2013 | Greenhalgh et al. |
| 2013/0096683 A1 | 4/2013 | Kube |
| 2013/0116793 A1 | 5/2013 | Kloss |
| 2013/0123850 A1 | 5/2013 | Schoenefeld et al. |
| 2013/0123935 A1 | 5/2013 | Hunt et al. |
| 2013/0131678 A1 | 5/2013 | Dahners |
| 2013/0144343 A1 | 6/2013 | Arnett et al. |
| 2013/0158609 A1 | 6/2013 | Mikhail et al. |
| 2013/0172736 A1 | 7/2013 | Abdou |
| 2013/0190614 A1 | 7/2013 | Swofford |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1 | 8/2013 | Hunt |
| 2013/0226301 A1 | 8/2013 | Reiley |
| 2013/0231746 A1 | 9/2013 | Ginn et al. |
| 2013/0237988 A1 | 9/2013 | Mauldin |
| 2013/0238031 A1 | 9/2013 | Reiley |
| 2013/0245703 A1 | 9/2013 | Warren et al. |
| 2013/0245763 A1 | 9/2013 | Mauldin |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0296953 A1 | 11/2013 | Mauldin et al. |
| 2014/0012340 A1 | 1/2014 | Beck et al. |
| 2014/0031934 A1 | 1/2014 | Trieu |
| 2014/0031935 A1 | 1/2014 | Donner et al. |
| 2014/0031939 A1 | 1/2014 | Wolfe et al. |
| 2014/0046380 A1 | 2/2014 | Asfora |
| 2014/0074175 A1 | 3/2014 | Ehler et al. |
| 2014/0088596 A1 | 3/2014 | Assell et al. |
| 2014/0088707 A1 | 3/2014 | Donner et al. |
| 2014/0121776 A1 | 5/2014 | Hunt |
| 2014/0135927 A1 | 5/2014 | Pavlov et al. |
| 2014/0142700 A1 | 5/2014 | Donner et al. |
| 2014/0200618 A1 | 7/2014 | Donner et al. |
| 2014/0207240 A1 | 7/2014 | Stoffman et al. |
| 2014/0222150 A1 | 8/2014 | Reiley |
| 2014/0249589 A1 | 9/2014 | Reiley et al. |
| 2014/0257294 A1 | 9/2014 | Gedet et al. |
| 2014/0257408 A1 | 9/2014 | Trieu et al. |
| 2014/0257415 A1 | 9/2014 | Reiley |
| 2014/0276846 A1 | 9/2014 | Mauldin et al. |
| 2014/0276851 A1 | 9/2014 | Schneider et al. |
| 2014/0277165 A1 | 9/2014 | Katzman et al. |
| 2014/0277460 A1 | 9/2014 | Schifano et al. |
| 2014/0277462 A1 | 9/2014 | Yerby et al. |
| 2014/0277463 A1 | 9/2014 | Yerby et al. |
| 2014/0288605 A1 | 9/2014 | Mesiwala et al. |
| 2014/0288649 A1 | 9/2014 | Hunt |
| 2014/0288650 A1 | 9/2014 | Hunt |
| 2014/0296982 A1 | 10/2014 | Cheng |
| 2014/0330382 A1 | 11/2014 | Mauldin |
| 2014/0364917 A1 | 12/2014 | Sandstrom et al. |
| 2015/0005832 A1 | 1/2015 | Reiley |
| 2015/0012051 A1 | 1/2015 | Warren et al. |
| 2015/0039037 A1 | 2/2015 | Donner et al. |
| 2015/0080951 A1 | 3/2015 | Yeh |
| 2015/0080972 A1 | 3/2015 | Chin et al. |
| 2015/0094765 A1 | 4/2015 | Donner et al. |
| 2015/0105828 A1 | 4/2015 | Reckling et al. |
| 2015/0112444 A1 | 4/2015 | Aksu |
| 2015/0150683 A1 | 6/2015 | Donner et al. |
| 2015/0173805 A1 | 6/2015 | Donner et al. |
| 2015/0173904 A1 | 6/2015 | Stark |
| 2015/0182268 A1 | 7/2015 | Donner et al. |
| 2015/0190149 A1 | 7/2015 | Assell et al. |
| 2015/0190187 A1 | 7/2015 | Parent et al. |
| 2015/0216566 A1 | 8/2015 | Mikhail et al. |
| 2015/0238203 A1 | 8/2015 | Asfora |
| 2015/0238205 A1 | 8/2015 | Reiley |
| 2015/0250595 A1 | 9/2015 | Mauldin et al. |
| 2015/0250611 A1 | 9/2015 | Schifano et al. |
| 2015/0250612 A1 | 9/2015 | Schifano |
| 2015/0313720 A1 | 11/2015 | Lorio |
| 2015/0320450 A1 | 11/2015 | Mootien et al. |
| 2015/0320451 A1 | 11/2015 | Mootien et al. |
| 2015/0320469 A1 | 11/2015 | Biedermann et al. |
| 2015/0342753 A1 | 12/2015 | Donner et al. |
| 2015/0351923 A1 | 12/2015 | Emstad |
| 2016/0000488 A1 | 1/2016 | Cross, III |
| 2016/0022429 A1 | 1/2016 | Greenhalgh et al. |
| 2016/0095721 A1 | 4/2016 | Schell et al. |
| 2016/0100870 A1 | 4/2016 | Lavigne et al. |
| 2016/0106477 A1 | 4/2016 | Hynes et al. |
| 2016/0106479 A1 | 4/2016 | Hynes et al. |
| 2016/0120661 A1 | 5/2016 | Schell et al. |
| 2016/0143671 A1 | 5/2016 | Jimenez |
| 2016/0175113 A1 | 6/2016 | Lins |
| 2016/0184103 A1 | 6/2016 | Fonte et al. |
| 2016/0242820 A1 | 8/2016 | Whipple et al. |
| 2016/0249940 A1 | 9/2016 | Stark |
| 2016/0287301 A1 | 10/2016 | Mehl et al. |
| 2016/0310188 A1 | 10/2016 | Marino et al. |
| 2016/0310197 A1 | 10/2016 | Black et al. |
| 2016/0324643 A1 | 11/2016 | Donner et al. |
| 2016/0374727 A1 | 12/2016 | Greenhalgh et al. |
| 2017/0020585 A1 | 1/2017 | Harshman et al. |
| 2017/0049488 A1 | 2/2017 | Vestgaarden |
| 2017/0128214 A1 | 5/2017 | Mayer |
| 2017/0135733 A1 | 5/2017 | Donner et al. |
| 2017/0143513 A1 | 5/2017 | Sandstrom et al. |
| 2017/0209155 A1 | 7/2017 | Petersen |
| 2017/0224393 A1 | 8/2017 | Lavigne et al. |
| 2017/0246000 A1 | 8/2017 | Pavlov et al. |
| 2017/0273729 A1 | 9/2017 | Reiley |
| 2018/0104071 A1 | 4/2018 | Reckling et al. |

FOREIGN PATENT DOCUMENTS

| | | |
|---|---|---|
| CN | 1909848 A | 2/2007 |
| CN | 101795632 A | 8/2010 |
| CN | 102361601 A | 2/2012 |
| EP | 1287796 A1 | 3/2003 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |
| JP | 11318931 A | 11/1999 |
| JP | 2002509753 A | 4/2002 |
| JP | 2003511198 A | 3/2003 |
| JP | 2003533329 A | 11/2003 |
| JP | 2003534046 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2008540036 A | 11/2008 |
| JP | 2009521990 A | 6/2009 |
| JP | 2010137016 A | 6/2010 |
| WO | WO97/31517 A2 | 8/1997 |
| WO | WO 01/17445 A1 | 3/2001 |
| WO | WO02/38054 | 5/2002 |
| WO | WO03/007839 A2 | 1/2003 |
| WO | WO04/02344 | 1/2004 |
| WO | WO2004/043277 A1 | 5/2004 |
| WO | WO2005/009729 A2 | 2/2005 |
| WO | WO2006/003316 | 1/2006 |
| WO | WO2006/023793 A2 | 3/2006 |
| WO | WO2009/029074 A1 | 3/2009 |
| WO | WO2010/105196 A1 | 9/2010 |

(56) References Cited

FOREIGN PATENT DOCUMENTS

| WO | WO2011/110865 A2 | 9/2011 |
|---|---|---|
| WO | WO2011/149557 A1 | 12/2011 |
| WO | WO2013/000071 A1 | 1/2013 |
| WO | WO2013/119907 A1 | 8/2013 |

OTHER PUBLICATIONS

Schneider et al.; U.S. Appl. No. 14/859,005 entitled "Matrix implant," filed Sep. 18, 2015.

Acumed; Acutrak Headless Compressioin Screw (product information); 12 pgs; © 2005; retrieved Sep. 25, 2014 from http://www.rcsed.ac.uk/fellows/Ivanrensburg/classification/surgtech/acumed/manuals/acutrak-brochure%200311.pdf.

Al-Khayer et al.; Percutaneous sacroiliac joint arthrodesis, a novel technique; J Spinal Disord Tech; vol. 21; No. 5; pp. 359-363; Jul. 2008.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Wise et al.; Minimally invasive sacroiliac arthrodesis, outcomes of a new technique; J Spinal Disord Tech; vol. 21; No. 8; pp. 579-584; Dec. 2008.

Sand et al.; U.S. Appl. No. 15/085,765 entitled "Neuromonitoring systems and methods for bone fixation or fusion procedures," filed Mar. 30, 2016.

Reiley et al.; U.S. Appl. No. 15/195,955 entitled "Apparatus, systems, and methods for the fixation or fusion of bone," filed Jun. 28, 2016.

Mauldin et al.; U.S. Appl. No. 15/208,588 entitled "System, device, and methods for joint fusion," filed Jul. 12, 2016.

Lu et al.; Mechanical properties of porous materials; Journal of Porous Materials; 6(4); pp. 359-368; Nov. 1, 1999.

Reiley et al.; U.S. Appl. No. 15/461,304 entitled "Systems and methods for the fixation or fusion of bone," filed Mar. 16, 2017.

Schneider et al.; U.S. Appl. No. 15/593,208 entitled "Matrix implant," filed May 11, 2017.

Mesiwala et al.; U.S. Appl. No. 15/903,410 entitled "Implants for spinal fixation or fusion," filed Feb. 23, 2018.

\* cited by examiner

(Anterior)

(Posterior)

| | | |
|---|---|---|
| Standard 7.0 mm Inscribed X 55 mm Length | | FIG. 7A |
| 7.5 mm Inscribed X 55 mm Length | | FIG. 7B |
| 7.5 mm Inscribed X 55 mm Length 30 deg fenestrations | | FIG. 7C |
| 7.5 mm Inscribed X 55 mm Length Distal end channel fenestrations concept 1 | | FIG. 7D |
| 7.5 mm Inscribed X 55 mm Length Distal end channel fenestrations concept 2 | | FIG. 7E |
| 7.5 mm Inscribed X 55 mm Length 90 deg circular fenestrations | | FIG. 7F |
| 7.5 mm Inscribed X 55 mm Length 15 deg curve | | FIG. 7G |
| 7.5 mm Inscribed X 55 mm Length 15 deg curve - straight cannula | | FIG. 7H |
| Tapered Implant 8.5 mm Inscribed proximal end, 7.5 mm Inscribed distal end, 55 mm Length | | FIG. 7I |

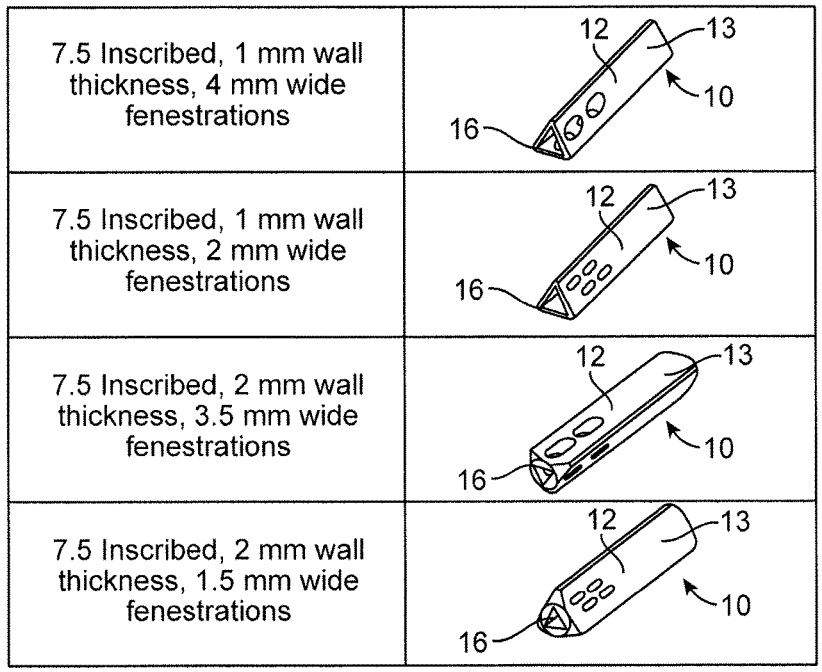
FIG. 7J
FIG. 7K
FIG. 7L
FIG. 7M
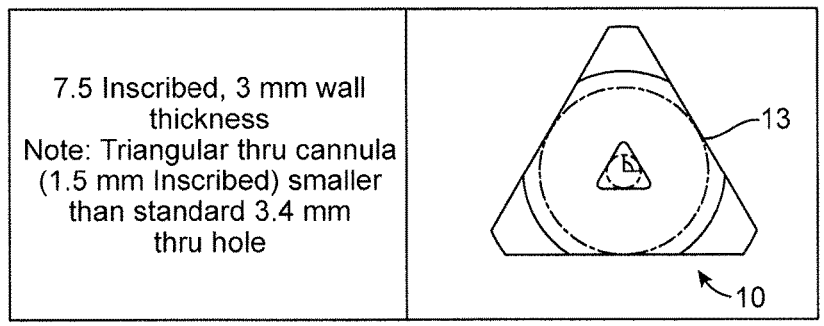
FIG. 8
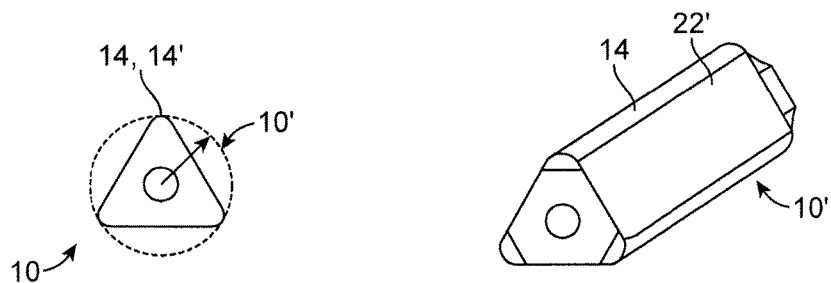
FIG. 9A  FIG. 9B

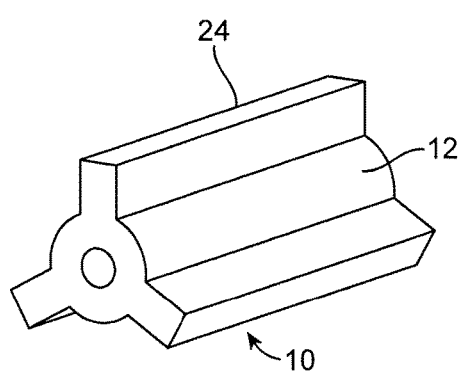
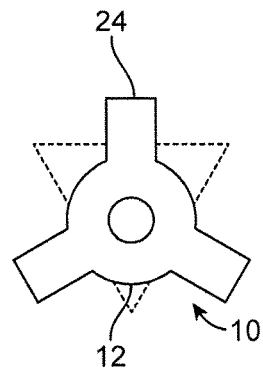
FIG. 10A  FIG. 10B
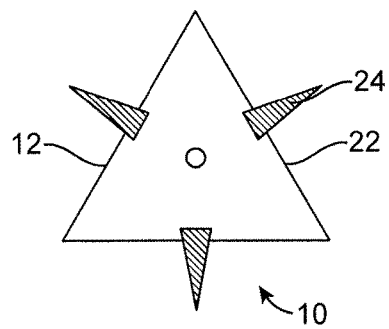
FIG. 10C
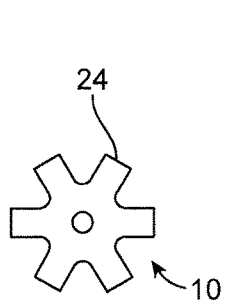
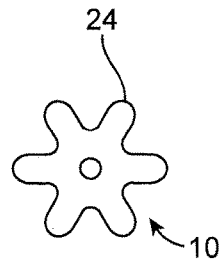
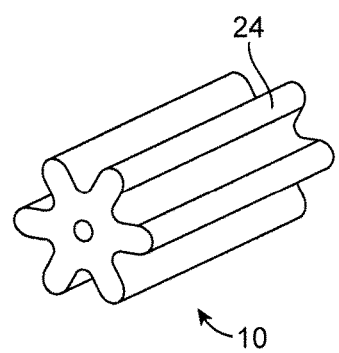
FIG. 11A  FIG. 11B  FIG. 11C

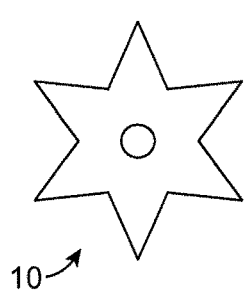 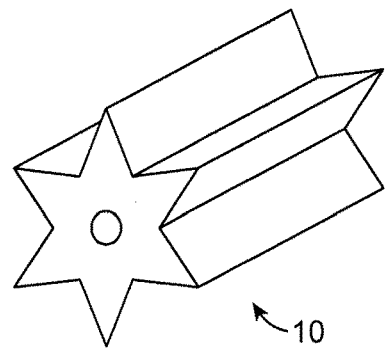
FIG. 12A  FIG. 12B
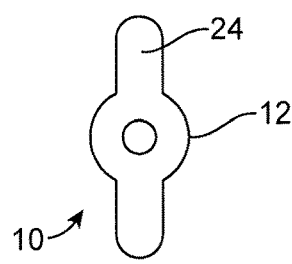 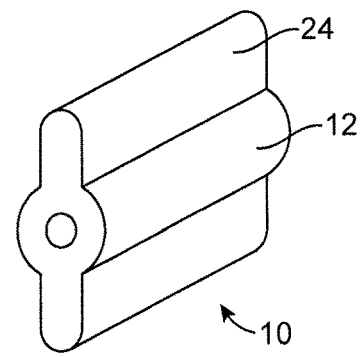
FIG. 13A  FIG. 13B
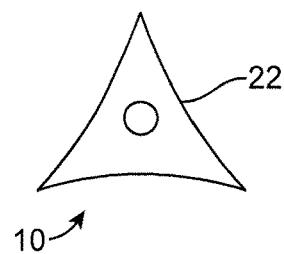 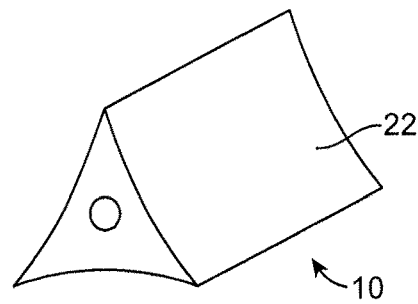
FIG. 14A  FIG. 14B

IMPLANTS FOR BONE FIXATION OR FUSION

CROSS REFERENCE TO RELATED APPLICATIONS

This application claim priority to U.S. Provisional Patent Application No. 62/052,318, filed Sep. 18, 2014, titled "IMPLANTS FOR BONE FIXATION OR FUSION," which is herein incorporated by reference in its entirety for all purposes.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate generally to bone implants that can be used to fuse two bone segments together.

BACKGROUND

Many types of hardware are available both for the fixation of bones that are fractured and for the fixation of bones that are to be fused (arthrodesed).

For example, the human hip girdle (see FIGS. 1 and 2) is made up of three large bones joined by three relatively immobile joints. One of the bones is called the sacrum and it lies at the bottom of the lumbar spine, where it connects with the L5 vertebra. The other two bones are commonly called "hip bones" and are technically referred to as the right ilium and-the left ilium. The sacrum connects with both hip bones at the sacroiliac joint (in shorthand, the SI-Joint).

The SI-Joint functions in the transmission of forces from the spine to the lower extremities, and vice-versa. The SI-Joint has been described as a pain generator for up to 22% of lower back pain patients.

To relieve pain generated from the SI-Joint, sacroiliac joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. Currently, screws and screws with plates are used for sacro-iliac fusion. At the same time the cartilage has to be removed from the "synovial joint" portion of the SI-Joint. This requires a large incision to approach the damaged, subluxed, dislocated, fractured, or degenerative joint. The large incision and removal of tissue can cause significant trauma to the patient, resulting in pain and increasing the time to heal after surgery.

In addition, screw type implants tend to be susceptible to rotation and loosening, especially in joints that are subjected to torsional forces, such as the SI-Joint. Excessive movement of the implant after implantation may result in the failure of the implant to incorporate and fuse with the bone, which may result in the need to remove and replace the failed implant.

Consequently, it would be desirable to provide an implant for bone fusion or fixation that resists rotation, can be implanted using a minimally invasive procedure, and/or that can be used to rescue a failed implant.

SUMMARY OF THE DISCLOSURE

The present invention relates generally to bone implants that can be used to fuse two bone segments together.

In some embodiments, an implant for the fixation or fusion of the SI-Joint is provided. The implant can include an elongate body having a longitudinal axis and a noncircular cross-sectional profile transverse to the longitudinal axis, the elongate body having a proximal end and a distal end, wherein the elongate body is curved along the longitudinal axis from the proximal end to the distal end of the elongate body.

In some embodiments, the noncircular cross-sectional profile has one or more apices. In some embodiments, the noncircular cross-sectional profile is substantially rectilinear. In some embodiments, the noncircular cross-sectional profile is triangular.

In some embodiments, the elongate body has a curvature between about 5 and 45 degrees. In some embodiments, the elongate body has a curvature between about 15 and 30 degrees.

In some embodiments, the elongate body has a plurality of fenestrations. In some embodiments, the fenestrations are located on a distal portion of the elongate body.

In some embodiments, a method of implanting a curved implant across a joint or fracture between a first bone segment and a second bone segment is provided. The method can include forming a curved insertion path from the first bone segment, across the joint or fracture between the first bone segment and the second bone segment, and to the second bone segment, wherein the curved insertion path has a predetermined radius of curvature along its length; and inserting a curved implant having a matching radius of curvature into the curved insertion path and into the first bone segment, across the joint or fracture, and into the second bone segment.

In some embodiments, the method further includes inserting a curved guidewire alone the curved insertion path. In some embodiments, the curved guidewire is rotated into the curved insertion path.

In some embodiments, the method further includes disposing a drill bit over the curved guidewire; and drilling a curved bore along the curved guidewire.

In some embodiments, the method further includes disposing a broach over the curved guidewire; and shaping the curved bore with the broach to form the insertion path.

In some embodiments, both the shaped insertion path and the curved implant have a transverse cross-sectional profile that is rectilinear. In some embodiments, both the shaped insertion path and the curved implant have a transverse cross-sectional profile that is defined by at least one apex. In some embodiments, both the shaped insertion path and the curved implant have a transverse cross-sectional profile that is triangular. In some embodiments, both the shaped insertion path and the curved implant have a transverse cross-sectional profile that is rectangular.

In some embodiments, the method further includes disposing a sharp tipped broach over the curved guidewire; and creating a curved and shaped bore along the curved guidewire using the sharp tipped broach.

In some embodiments, an implant for the fixation or fusion of the SI-Joint is provided. The implant can include an elongate body have a longitudinal axis and a noncircular cross-sectional profile transverse to the longitudinal axis, the elongate body having a proximal end and a distal end, wherein the elongate body comprises one or more faces that extend from the proximal end to the distal end of the elongate body, each face having a slot extending from the distal end of the elongate body towards the proximal end of the elongate body along the longitudinal axis; and a rib slidably disposed in each slot.

In some embodiments, the slot is selected from the group consisting of a dovetail slot and a t-slot.

In some embodiments, the rib is made of a material selected from the group consisting of bone graft, metal, metal alloy, hydroxyapatite, ceramic, and polymer.

In some embodiments, the elongate body has three faces and a triangular cross-sectional profile transverse to the longitudinal axis.

In some embodiments, the rib is wedge shaped.

In some embodiments, the rib is positioned in a central portion of the implant and offset from both the proximal end and the distal end of the elongate body.

In some embodiments, an implant for the fixation or fusion of the SI-Joint is provided. The implant can include an elongate body have a longitudinal axis and a noncircular cross-sectional profile transverse to the longitudinal axis having one or more apices, wherein a portion of the one or more apices is removed to form a face along the one or more apices, the face having a slot that extends along the longitudinal axis; and a rib slidably disposed in the slot.

In some embodiments, the rib is made of a material selected from the group consisting of bone graft, metal, metal alloy, hydroxyapatite, ceramic, and polymer.

In some embodiments, the rib is sized and configured to restore the shape of the removed portion of the one or more apices.

In some embodiments, an implant for the fixation or fusion of the SI-Joint is provided. The implant can include an elongate body have a longitudinal axis and a noncircular cross-sectional profile transverse to the longitudinal axis, the elongate body having a proximal end and a distal end, wherein the elongate body comprises one or more faces that extend from the proximal end to the distal end of the elongate body; an elongate rib disposed along the one or more faces of the elongate body; and a wire cage configured to secure the elongate rib to the elongate body.

In some embodiments, the wire cage comprises a first opening to receive the elongate body and a second opening to receive the elongate rib.

In some embodiments, an implant for the fixation or fusion of the SI-Joint is provided. The implant can include an elongate body have a longitudinal axis and a noncircular cross-sectional profile transverse to the longitudinal axis, the elongate body having a proximal end and a distal end, wherein the elongate body comprises one or more faces that extend from the proximal end to the distal end of the elongate body; and one or more fenestrations located on a distal portion of the elongate body.

In some embodiments, the one or more fenestrations are located along a central portion of the one or more faces of the elongate body.

In some embodiments, the elongate body comprises at least one apex and the one or more fenestrations are located at the distal end of the at least one apex.

In some embodiments, the one or more fenestrations are circular.

In some embodiments, the one or more fenestrations are oblong.

In some embodiments, the elongate body is tapered such that the distal end has a smaller diameter or width than the proximal end.

In some embodiments, the elongate body comprises a plurality of walls that form the one or more faces and define a lumen having a noncircular cross-sectional profile.

In some embodiments, the noncircular cross-sectional profile of both the elongate body and the lumen is triangular.

In some embodiments, the noncircular cross-sectional profile of both the elongate body and the lumen is rectangular.

In some embodiments, the elongate body is coated with hydroxyapatite.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 7A-7M illustrate perspective views of alternative embodiments of implants that can be used for the fusion or fixation of a joint or two bone segments.

FIG. 8 is a cross-sectional view of an embodiment of an implant having a triangular thru cannula.

FIGS. 9A-9B illustrate an embodiment of an implant with larger dimensions and truncated corners.

FIGS. 10A-10B illustrate an embodiment of an implant with a plurality of ribs.

FIG. 10C illustrates another embodiment of an implant with a plurality of ribs that are formed by osteoconductive materials such as bone, metal, metal alloy, ceramic, and polymer.

FIGS. 11A-11C illustrate additional embodiments of implants with ribs.

FIGS. 12A and 12B illustrate an embodiment of an implant with a double triangle cross-sectional profile.

FIGS. 13A and 13B illustrate another embodiment of an implant with ribs.

FIGS. 14A and 14B illustrate another embodiment of a triangular implant with curved sides.

DETAILED DESCRIPTION

Figure 1:
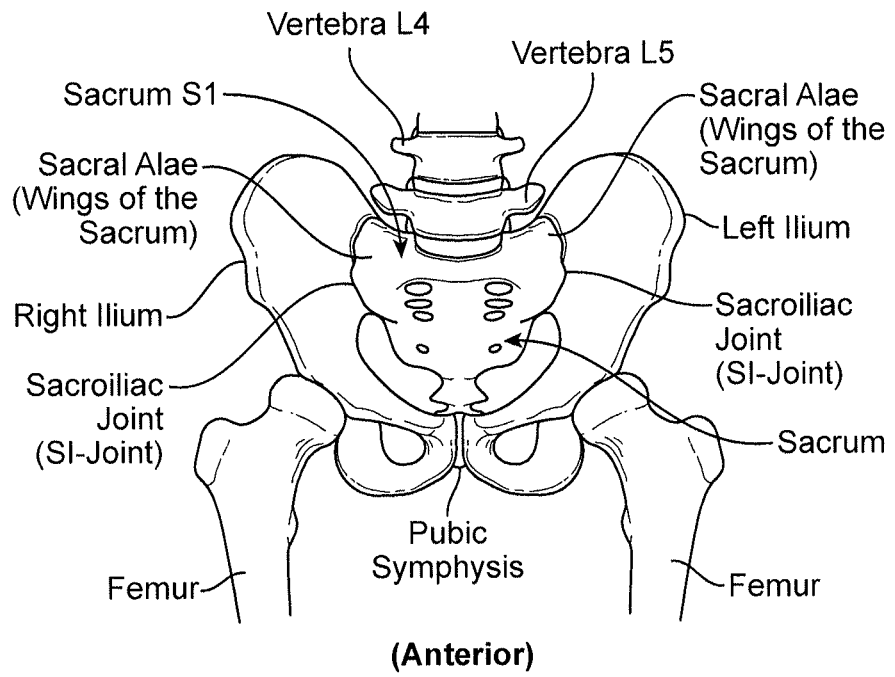
FIGS. 1 and 2 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).
Figure 2:
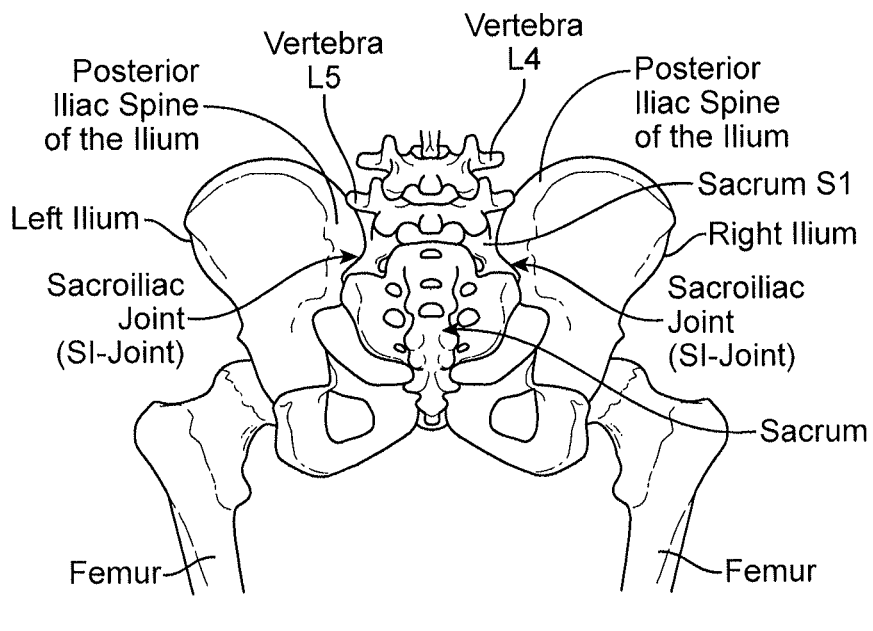
Figures 3, 4:
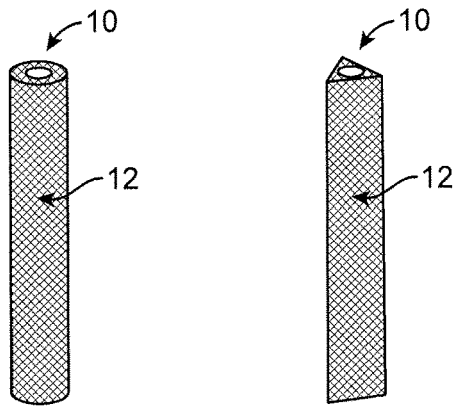
FIGS. 3 and 4 are embodiments of various straight implants that can be used for the fusion or fixation of a joint or two bone segments.

FIG. 3 and FIG. 4 illustrate straight implants 10 with a solid elongate body 12 that can be used for the fixation or fusion of two bone segments. The implant 10 shown in FIG. 3 is cylindrical and can optionally have screw threads along the exterior of the implant body. As mentioned above, cylindrical screw type implants can suffer from excessive rotation. One solution to this problem is the implant 10 in FIG. 4, which has a non-cylindrical cross-sectional area. For example, as shown, the implant 10 can have a triangular cross-sectional area, although other rectilinear cross-sectional profiles may be used as well, including rectangular, hexagonal and the like. Non-cylindrical implants need not have a strict rectilinear cross-sectional profile in order to resist rotation. A cross-sectional area that is non-circular will generally suffice. For example, a tear drop shaped cross-sectional area, or a cross-sectional area with at least one apex, can resist rotation. Other non-circular cross-sectional geometries that may not have a rectilinear component can also work, such as oval cross-sections.

Figure 5:
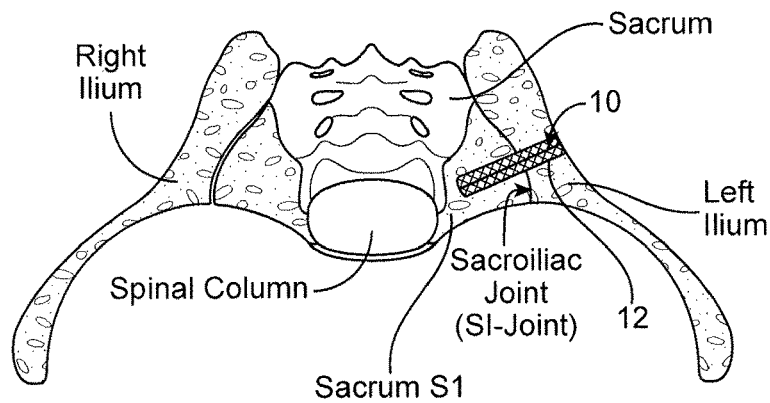
FIG. 5 illustrates an axial section view of the SI-Joint with an implant for the fixation of the SI-Joint using a lateral approach that goes laterally through the ilium, the SI-Joint, and into the sacrum.
Figure 6:
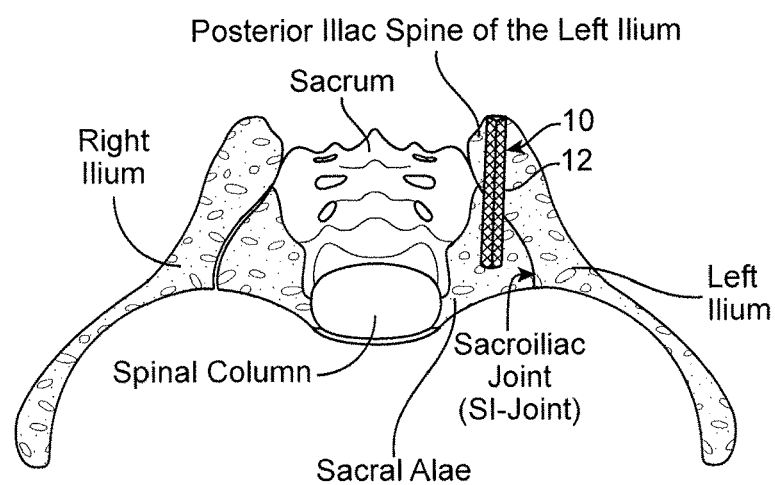
FIG. 6 illustrates an axial section view of the SI-Joint with an implant for the fixation of the SI-Joint using a posterolateral approach entering from the posterior iliac spine of the ilium, angling through the SI-Joint, and terminating in the sacral alae.

FIG. 5 illustrates insertion of the implant 10 of FIG. 4 across the SI-Joint using a lateral approach that goes laterally through the ilium, across the SI-Joint, and into the sacrum. FIG. 6 illustrates insertion of the same implant across the SI-Joint using a postero-lateral approach entering from the posterior iliac spine of the ilium, angling through the SI-Joint, and terminating in the sacral alae. Many of the implants described herein can be inserted across the SI-Joint in a similar manner.

Implant Variations

FIGS. 7A and 7B illustrate implants 10 that are similar to the implant 10 illustrated in FIG. 4. The implants 10 in FIGS. 7A and 7B have an elongate body 12 and a triangular cross-sectional area transverse to a longitudinal axis that extends through the elongate body 12. The corners or apices 14 of the implant 10 can be rounded and the distal ends 16 of the implants can be tapered to facilitate insertion. The implants 10 can have a cylindrical lumen 18 that extends the length of the elongate body 12. The difference between the implants 10 in FIGS. 7A and 7B is the size of the implants, in particular with respect to the implant diameter, which can be described with reference to an inscribed circle within the cross-sectional area of the implant. The implant 10 in FIG. 7A has a 7.0 mm inscribed diameter, while the implant in FIG. 7B has a 7.5 mm inscribed diameter. As illustrated, the length of both the implants is 55 mm. It should be noted that the dimensions of the implants described herein can vary. For example, the inscribed diameter can vary between about 3 mm to 14 mm, and the length can vary between about 20 mm to 90 mm, or between about 20 mm to 220 mm.

FIGS. 7C-7F illustrate implants 10 with fenestrations 20. FIG. 7C illustrates an implant 10 that is similar to the implant described in FIG. 7B except that this implant also has elliptical fenestrations 20 located in the distal portion of the implant. Distal fenestrations will preferentially allow for bony through-growth within the sacral portion of the implant. The elliptical fenestrations 20 can be positioned in the center of each face 22 of the elongate body 12 such that the major axis of the ellipse is aligned with the longitudinal axis of the implant. Each face 22 can have between 1 to 4 fenestrations. As illustrated, each face 22 has two fenestrations 20 which are 30 degree ellipses. The ellipse can have a degree between about 5 and 90 degrees, where the degree specifies the angle with which a circle is viewed, meaning a 90 degree ellipse specifies a circle while a zero degree ellipse specifies a line. In FIG. 7D, the fenestrations 20 are still centered on each face but are moved all the way to the distal end 16 of the implant such that the fenestrations 20 extend proximally along the face 22 from the distal end 16. In FIG. 7E, the fenestrations 20 are located at the distal end 16 of the implant but are located at the apices 14 of the implant rather than the center of each face 22. In FIG. 7F, the fenestrations 20 are circular.

The shape, size, number and location of the fenestrations can affect the strength of the implant and its ability to resist or tolerate compressive, tensile, bending, torsional, and shear forces. Other fenestration shapes include rectilinear shapes, such as square, rectangular, triangular, and the like. Other locations for the fenestrations include the middle and proximal portions of the implant. Other fenestration locations will allow for bony through-growth in those portions of the implant, such as the ilium portion of the implant. The depth of the fenestrations can penetrate to the lumen or can stop before reaching the lumen. In some embodiments, the size of the fenestrations facilitates the use of bone graft material or other biologic aids. For example, the fenestrations can be between about 1-10 mm in length and about 1-5 mm in width.

FIGS. 7G and 7H illustrate curved implants 10, where the elongate body 12 has a curvature along its length from the proximal end of the implant to the distal end of the implant. The arc can range from 20 mm to 90 mm, and the radius of curvature can range from about 25 mm to about 1000 mm. The arc can be between about 5 to 45 degrees, or about 15 to 30 degrees. The curved implants 10 can have a cross-sectional area that includes one or more apices. For example, as illustrated, the overall cross-sectional area is triangular. In some embodiments, the curved implant 10 can have an overall cross-sectional area that is circular, such that the implant can be a curved rod. The curved implant 10 can have a curved lumen 18 with a curvature that matches the curvature of the implant, as illustrated in FIG. 7G. Alternatively, the curved implant 10 can have a straight lumen 18, as illustrated in FIG. 7H. In other embodiments, the curved implant 10 can have a curved lumen 18 with a curvature that is different from the curvature of the implant 10. The curvature of the implant can improve resistance to twisting forces, rotation, and pull out forces as compared to a straight rod. The method of implantation of the curved implants 10 may be substantially different from the implantation of straight implants, as further described below. Curved implants have also been described in co-pending U.S. patent application No. 14/216,938, which is herein incorporated by reference in its entirety for all purposes.

FIG. 7I illustrates an implant 10 that can have a tapered elongate body 12. The elongate body 12 can be tapered from the proximal end 15 to the distal end 16 of the implant. In some embodiments, the taper can be constant such that the faces 22 of the implant are flat. In other embodiments, the taper can result in concave or convex faces 22. For example, in some embodiments, the proximal end 15 can inscribe an 8.5 mm diameter circle, while the distal end can inscribe a 7.5 mm circle. In some embodiments, the difference in diameters between the proximal end and the distal end can be between about 0.5 mm to about 3 mm, or between about 1-2 mm. The taper can facilitate the initial insertion of the implant 10 into a bore, while also providing enhanced securement and friction fit or press-fit within the bore as the wider portion of the implant is driven into the bore.

FIGS. 7J-7M illustrate implants 10 with a hollow interior in place of the lumen such that the elongate body 12 is formed by a plurality of walls. The walls can have a thickness between about 0.5 mm to about 5 mm, or between about 1 mm to about 3 mm. For example, the implants 10 illustrated in FIGS. 7J and 7K have a wall thickness of 1 mm while the implants 10 illustrated in FIGS. 7L and 7M have a wall thickness of 2 mm. The hollow interior of the implant 10 can be filled and packed with bone graft material and/or another biologic aid to promote bone growth into and throughout the implant 10. The biologic aid can contain bone growth promoters such as bone morphogenetic proteins (BMPs) and/or anti-inflammatory agents, analgesic agents, antibiotics, and anti-microbial agents. In addition, bone graft material and/or a biologic aid can be introduced into the bone cavity and/or the joint or space between the two bones through the hollow interior and fenestrations 20. The fenestrations can be between 1 to 10 mm in length. For example, as illustrated, the fenestrations 20 can be 1.5, 2, 3.5 or 4 mm in length. In some embodiments, the distal end 16 of the walls 13 can be sharpened into chisel or blade-like edges such that the implant can be driven into and through the bone at the implantation site without the need of a pre-formed bore. In some embodiments, a pilot bore can be drilled and the implant can be hammered or tapped into the pilot bore without the need of shaping the pilot bore with a broach. The thickness of the walls 13 can be designed to provide enough strength to accommodate the forces exerted on the implant after implantation. FIG. 8 illustrates a cross-sectional view of an implant 10 with 3 mm thick walls, which provides additional strength to the implant 10. A round guide pin can be used to guide placement of the implant 10, or alternatively, a triangular (or rectilinear or another geometry) pin can be used to guide implant placement. Using a triangular or rectilinear guide pin can allow the operator to align the rotational placement of the implant by simply aligning the guide pin. Implants with fenestrations and a hollow interior defined by a plurality of walls have also been described in U.S. Publication No. 2013/0296953, which is herein incorporated by reference in its entirety.

FIGS. 9A and 9B illustrate a series of implants 10, 10' where the tips of the apices 14, 14' can be aligned. The smaller of the two implants 10 can be a standard triangular or rectilinear implant as illustrated in solid lines in FIG. 9A, while the larger implant 10' is illustrated in dotted lines in the same figure. As illustrated, the apices 14, 14' of the two implants 10, 10' are located in the same location, but the apices 14' of the larger implant 10' are more rounded or blunt and the faces 22' are spaced further apart such that the larger implant 10' inscribes a larger circle than the smaller implant 10 even though the apices 14, 14' are located at the same location. In other embodiments, there can be some variation between the location of the apices while the other features are still retained, such as the rounder apices and larger inscribed circle. This geometry can reduce implant to implant interference when implanting a plurality of implants across the limited space of a single joint. In addition, this geometry may be particularly useful for the rescue of a failed implant where one implant needs to be replaced without interfering with the other neighboring implants. The replacement implant should be larger in size to ensure a tight fit into the replacement bore while also not extending too far as to interfere with neighboring implants.

Other implants that may be particularly suitable for the rescue of failed implants or can be used as new implants are shown in FIGS. 10A-13B. For example, FIGS. 10A and 10B illustrate a cylindrical implant 10 with a plurality of ribs 24 that extend from the elongate body 12 of the implant. As illustrated, the implant 10 can have a number of ribs 24 that equals the number of sides of the cavity or the implant that is being rescued or replaced. For example, a three rib 24 implant 10 can be used to rescue or replace a triangular implant or a cylindrical implant. The cylinder portion of the implant 10 can have a diameter that roughly matches the size of the inscribed circle of the triangular implant or the size of the cylindrical implant. In this arrangement, the ribs 24 can be located in bone while the cylindrical portion can be located in the cavity after the old implant is removed. In some embodiments, the ribs 24 can be about 1-5 mm wide and 2-8 mm high. The ribs 24 can have a rectilinear overall cross-sectional profile or can have a rounded profile or can have a profile that is a combination of the two.

FIG. 10C illustrates another embodiment of an implant 10 with a plurality of ribs 24. In this embodiment, the implant 10 has an elongate body 12 with a rectilinear overall cross-section profile, which can be triangular as shown, or can be rectangular or square or another shape. Each face 12 of the elongate body 12 can have a rib 24 which can be located along the center or central portion of the face 12. The ribs 24 can extend the full length of the elongate body or can extend only partially along the length of the elongate body. In some embodiments, the ribs 24 can extend from the proximal ends of the elongate body 12. In other embodiments, the ribs 24 can extend from the distal ends of the elongate body 12. In some embodiments, the ribs 24 can be located along a central portion of the elongate body 12 and be offset from both ends of the implant. The ribs 24 can be tapered to an edge such that the ribs are wedge shaped. The ribs 24 can be attached to the elongate body 12 in a variety of ways. For example, if the ribs 24 are made of a different material than the elongate body, such as being made from a bone graft material including cortical or dense cancellous bone, the ribs 24 can be attached using a dovetail joint or a t-slot fastener. If the ribs 24 are made of the same material as the elongate body 24, the ribs 24 can be attached as described above, or can be fabricated along with the body such that the ribs 24 are integral with the elongate body. The ribs can be made of a variety of materials including bone, metal, metal alloy, ceramic, hydroxyapatite and polymer. The ribs 24 can be designed to cross the joint or fracture during or after implantation.

Figure 10D:
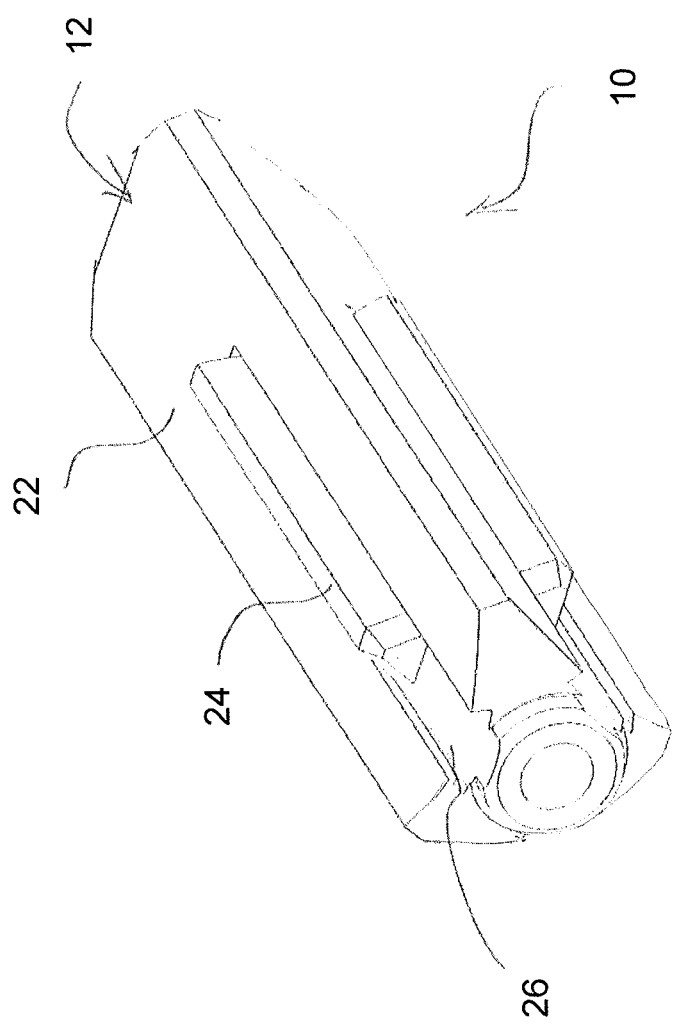
FIGS. 10D-10F illustrate additional embodiments of various implants with ribs.

FIG. 10D illustrates another embodiment of an implant with ribs similar to the embodiment shown in FIG. 10C. The implant 10 has dovetail grooves 26 that run along a length of the elongate body 12 of the implant 10. In this embodiment, the grooves 26 are located on and centered on the face 22 of the elongate body, extending from the distal end of the implant and extending towards the proximal end of the implant. In this embodiment, the grooves 26 terminate before reaching the proximal end of the implant so that when the ribs 24 are fully inserted into the dovetail groove, the ribs 24 are located along a central portion of the elongate body 12 such that the ribs 24 are offset from both ends of the implant. The ribs 24 are designed to fit within the dovetail groove and extend outwards in a wedge shape. In this embodiment, the ribs 24 can terminate in a flat or rounded end instead of a point. The distal ends of both the implant and the ribs can be tapered to narrow in the distal direction to facilitate insertion of the implant. In some embodiments, the width of the base of the rib that fits into the groove can be about ⅛ to ¾, or about ¼ to ½ the width of the face of the implant.

Figure 10E:
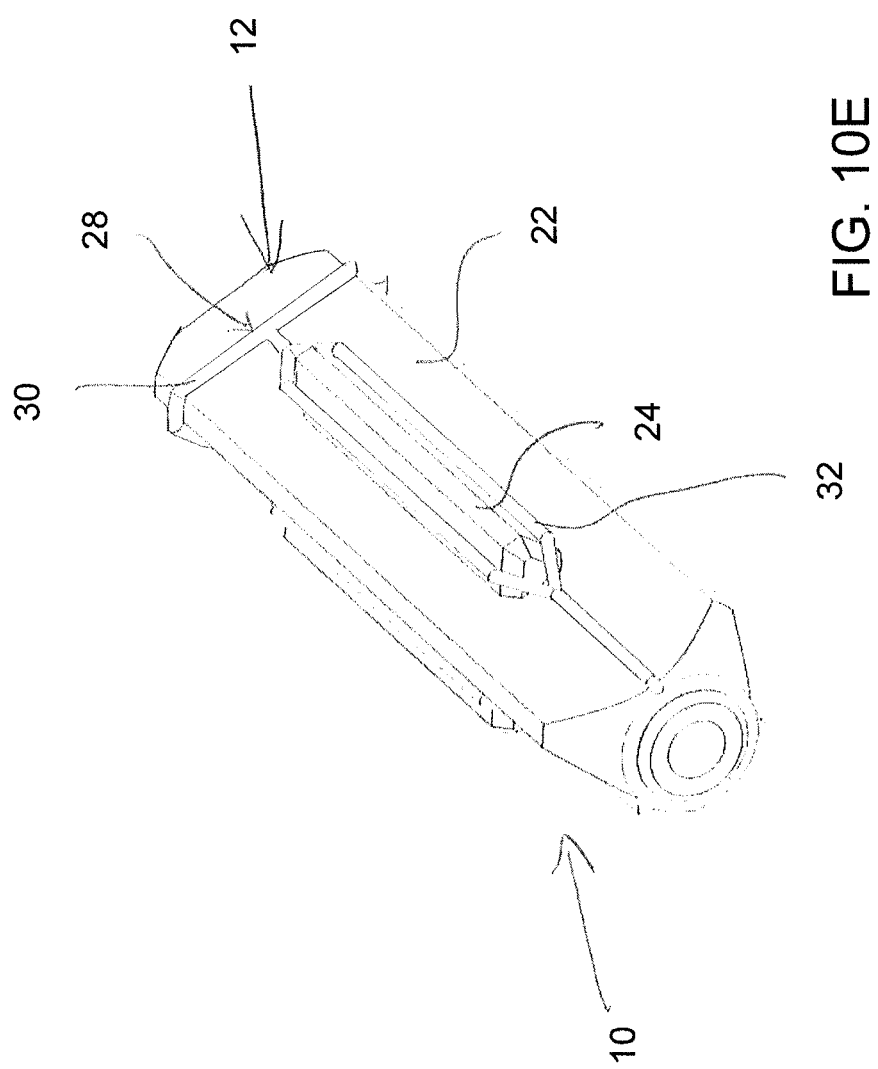

FIG. 10E illustrates another embodiment of an implant with ribs. The ribs 24 can be located along the faces 22 of the implant 10, and can have a similar shape and configuration as the ribs described in FIG. 10D. However, instead of using a dovetail groove to secure the ribs 24, the implant 10 has a frame structure 28 for securing the ribs 24 to the faces 22 of the implant. The frame structure 28 can have an implant securing portion 30 that can be attached to the implant. For example, the implant securing portion 30 can be sized and shaped to receive the implant, or in other words, it can have an opening that matches the cross-sectional profile of the implant. The implant securing portion 30 can also have one or more rib securing portions 32 for securing the ribs 24 against the faces 22 of the implant. The rib securing portion 32 can have an opening sized and shaped to receive a portion of the rib 24. For an elongate, wedge shaped rib, the opening of the rib securing portion can have a length at least equal to the length of the rib while having a width that is less than the width of the base of the rib. Such a configuration allows the rib to extend partially through the opening of the rib securing portion. In some embodiments, the rib securing portions 32 can be biased towards the faces 22 of the implant such that when the ribs are secured within the rib securing portions, the ribs are pressed against the faces of the implant. The frame structure 28 can be configured to center the ribs on the faces of the implant. In some embodiments, the frame structure 28 can be made of a wire or ribbon cage structure that can slide over the implant to secure one or more ribs to the faces of the implant. The frame can be made of a metal, plastic, or composite material. In some embodiments, the frame can be secured to the implant with an adhesive, by welding it to the implant, or by fitting the frame in grooves or slots in the implant. Similarly, the ribs can also be secured to the implant and/or frame using adhesives, by welding, or by fitting it into a groove or slot.

Figure 10F:
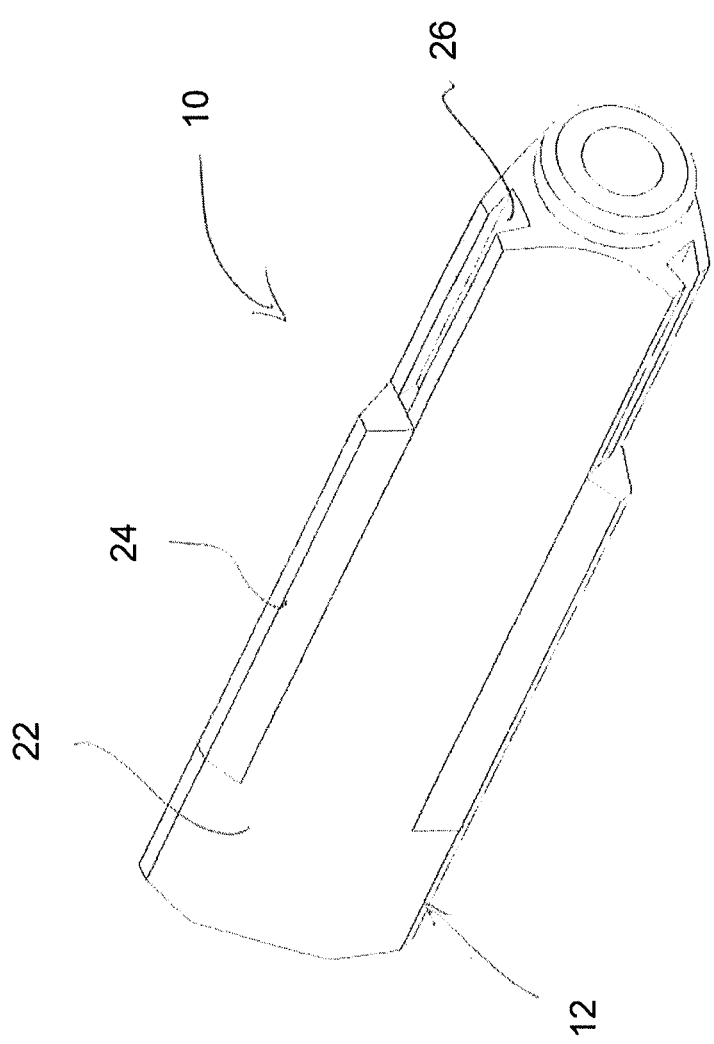

FIG. 10F illustrates another embodiment of an implant with ribs, this time with the ribs located along the apices of the implant. In this embodiment in particular, the ribs 24 are generally made of a different material than the implant. For example, the ribs can be made of a bone graft material, such as autograft or allograft bone, metal, metal alloy, hydroxyapatite, a ceramic, a polymer, or some other material or a combination of materials. However, in other embodiments, the ribs can be made of the same or similar material as the implant. In this embodiment, a portion of each apex can be removed to allow the ribs to form the apices of the implant. For example, the distal and central portion of the apices can be removed, leaving a proximal portion of the apices to remain. In other embodiments, the entire apex can be removed. In other embodiments, the proximal and central portion of the apices can be removed, leaving a distal portion of the apices to remain. A dovetail groove 26 can extend along the removed portion of the apex. The ribs 24 can have a trapezoidal joint portion extending along the length of the ribs that fits within the dovetail groove 26 in a sliding dovetail joint. The portion of the rib 24 extending outside the joint can by sized and shaped to replace a missing portion of the apex. For example, the outside portion of the rib 24 can be triangular or trapezoidal shaped with a rounded off end and with sides that are flush with the faces 22 of the implant. The distal end of the rib 24 can be tapered or beveled.

FIGS. 11A-11C illustrated alternative embodiments of implants 10 with ribs 24. As illustrated, the implants 10 can have a plurality of ribs 24, or even a single rib. The ribs 24 can have a rectilinear overall cross-sectional profile or a curvilinear overall cross-sectional profile or a combination of the two.

FIGS. 12A and 12B illustrate an embodiment of an implant with a double triangle overall cross-sectional profile. This implant 10 may be particularly suitable for the rescue of a failed triangular implant. The double triangle implant 10 can be inserted into the cavity such that one of the two triangles is aligned with the cavity while the other triangle penetrates into the bone.

FIGS. 13A and 13B illustrates a cylindrical implant 10 with two large curvilinear ribs 24 that are located on opposite sides of the elongate body 12 of the implant 10. This embodiment can be used to rescue a cylindrical implant or a rectilinear implant as long as the ribs 24 are large enough to extend into bone.

FIGS. 14A and 14B illustrate an implant 10 with a triangular overall cross-sectional profile with curved sides or faces 22. The faces 22 can be concave as shown, or can alternatively be convex. An advantage of a convex design is bony preservation, i.e. less bone is removed to prepare the hole for this implant. An advantage of the concave or convex design is the increased surface area compared to an implant with flat surfaces. In some embodiments, the implant 10 can have additional sides or faces or fewer sides or faces. In some embodiments, some of the sides or faces are convex, some of the sides or faces are concave, and/or some of the sides and faces are flat.

Figures 15A, 15B:
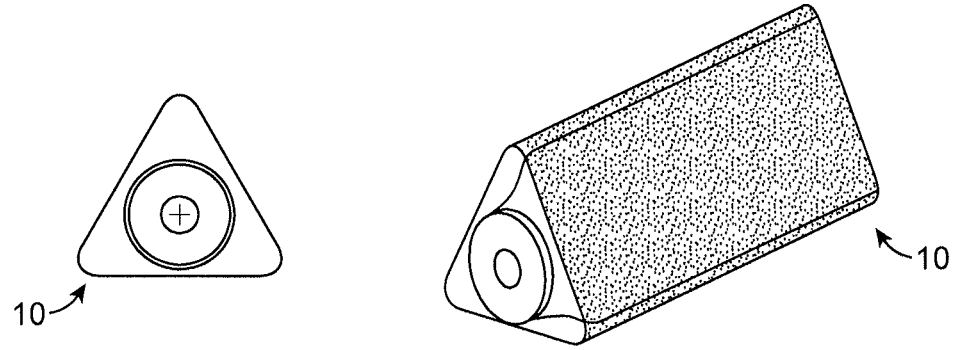
FIGS. 15A and 15B illustrate an embodiments of an implant that has been coated with a titanium plasma spray and a hydroxyapatite coating.

FIGS. 15A and 15B illustrate an implant 10 that is coated with both a titanium plasma spray (TPS) and a hydroxyapatite coating. The TPS coating can provide a roughened and porous surface that facilitates and promotes bony ingrowth and can also provide a roughened surface that can serve as a substrate for the hydroxyapatite coating, which can further promote bony ingrowth and fusion with native bone. The hydroxyapatite coating can be applied over the entire implant, including the exterior surfaces and the interior surfaces, or the hydroxyapatite coating can be applied preferentially on certain surfaces, such as the exterior surface or even just the distal, middle, and/or proximal portions of the implant. The thickness of the TPS coating can be between about 100 and 1500 μm and the thickness of the hydroxyapatite coating can be between about 10 and 1000 μm. These coatings can be applied on any of the implants described herein including implants that are manufactured via 3-D printing or additive manufacturing.

Methods of Implantation

The methods of implantation of the various implants described herein are described in U.S. Patent Publication No. 2011/0087294, U.S. Pat. Nos. 8,425,570, 8,444,693, 8,414,648, and 8,470,004, and co-pending U.S. Provisional Application No. 61/891,326, each of which is herein incorporated by reference in its entirety for all purposes. These methods are particularly suited for use with straight implants.

Figure 17A:
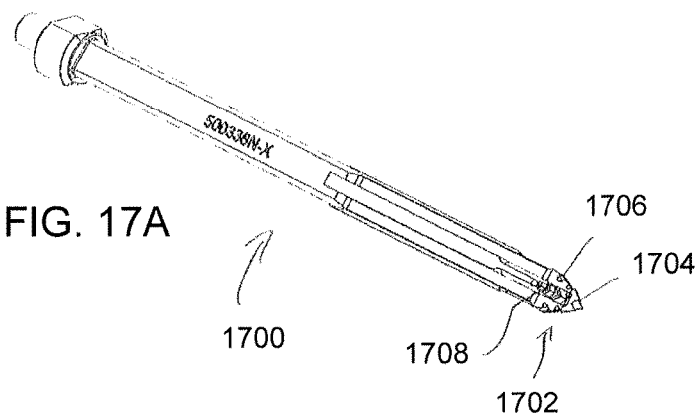
FIGS. 17A-17C illustrate various views of a modified broach for creating a bore in bone suitable for receiving an implant with ribs.
Figure 17B:
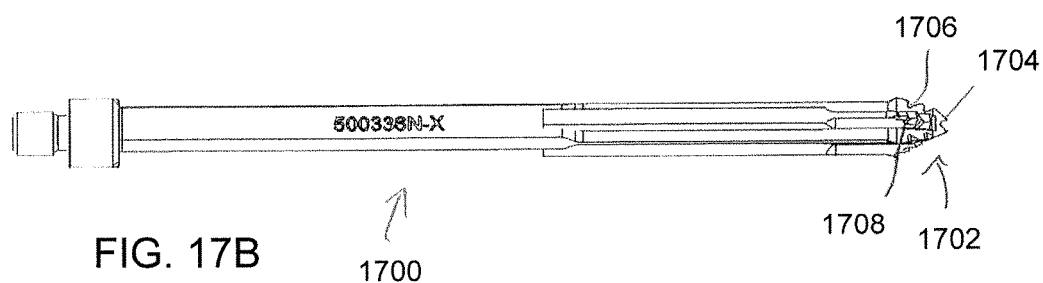
Figure 17C:
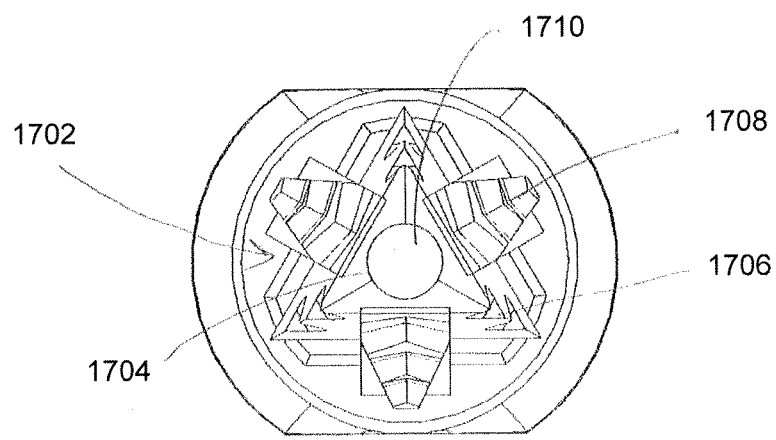

Referring to FIGS. 17A-17C, a modified broach 1700 can be used to cut out and/or shape a bore for an implant with ribs, such as the implants described in FIGS. 10C-10E, for example. The broach can have a distal cutting head portion 1702 with sharp, pointed cutting elements 1704 at the distal end of the cutting head portion. This allows the broach to be used both with a drill to shape a pilot bore and without a drill to form the bore directly over the guide pin. A plurality of cutting elements 1706 are arranged in a progressively expanding outward pattern that matches the cross-sectional shape and size of the implant. In addition, secondary cutting elements 1708, which may be removably or permanently attached to the broach, can be added to cutting head 1702 to cut out slots for the ribs of the implant. The secondary cutting elements 1708 can be positioned between the apices of the cutting elements 1706 to match the position of the ribs on the implant. The secondary cutting elements 1708 can also have a plurality of staggered cutting edges and surfaces that successively increase in size and shape to match the size and shape of the ribs of the implant. The broach 1700 can also have a lumen 1710 extending along the length of the broach for receiving a guide pin. The broach can be used with a modified soft tissue protector that allows the broach to pass through with the secondary cutting elements.

The curved implants illustrated in FIGS. 7G and 7H may require modifications to the method of insertion protocols. Because the implants are curved, it may not be possible or desirable to attempt to hammer or tap the implant into the bone along a straight path using a straight guide pin, a straight drill, a straight broach and the like. Instead, it may be desirable to create and form a curved insertion path that matches the curvature of the implant.

Figure 16:
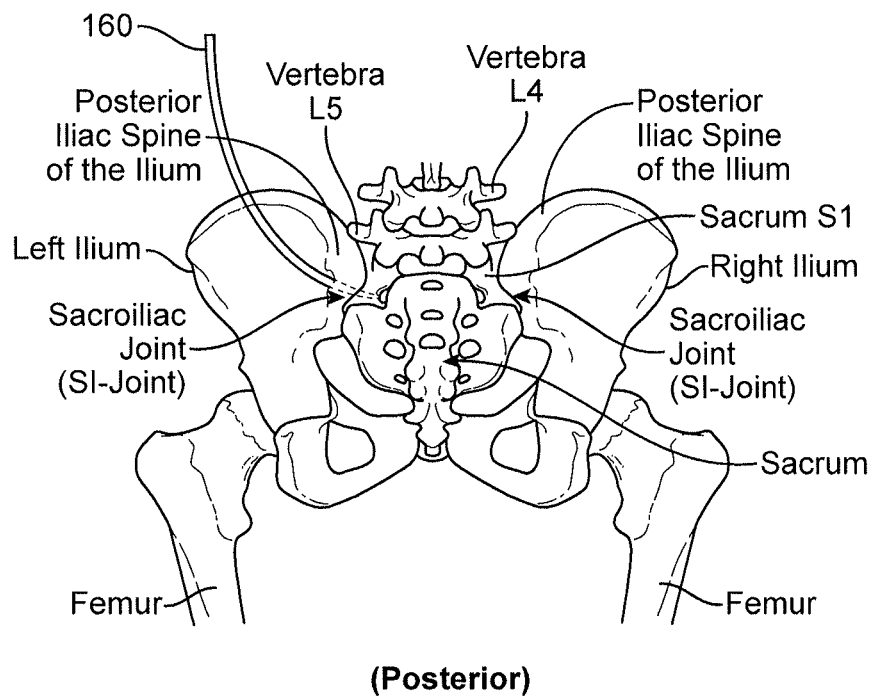
FIG. 16 illustrates the use of curved tooling for the implantation of a curved implant.

For example, the tooling used to create the curved insertion path can have a radius of curvature that matches the radius of curvature of the implant. For example, some or all of the tooling and the implant can have a matching radius of curvature, as shown in FIG. 16. The tooling, which can include a guide pin or guidewire 160, a tool guide, a drill bit, a broach, and impact hammer and the like can be rotatably secured by an arm with a length equal to the radius of curvature, with one end of the arm attached to a pivot and the other end used to secure the tools and/or implant.

The rotating arm can be used to drive a curved guide pin into the bone to create a curved path through the bone, such as the ilium and the sacrum. A relatively short drill bit with a lumen for receiving the guide pin can be disposed over the curved guide pin to drill out a curved pilot bore. In some embodiments, the drill bit can be secured by the pivoting arm at the end of a curved guide and can be used to drill the curved pilot bore without the insertion of the curved guide pin.

For a curved implant with a circular overall cross section, the curved implant can then be advanced over the curved guide pin and into the curved insertion path that is formed by the curved pilot bore. In some embodiments, the curved implant can be held by the pivoting arm and inserted into the curved insertion path without the aid of a guide pin by rotating the curved arm.

For a rectilinear implant or more broadly a noncircular implant, the curved pilot bore can be shaped using an appropriately shaped broach that matches the cross-sectional shape of the implant. A curved broach, or a short broach, can be advanced over the curved guide pin if present, otherwise the curved broach or short broach can be held in the pivoting arm and advanced through the pilot bore by rotation of the pivoting arm. As the broach is advanced, it shapes the pilot bore into a shape that matches the shape of the implant. In some embodiments, a broach with a sharp distal tip can be used to create a bore without the need of drilling out a pilot bore. Examples of sharp tipped broaches are disclosed in U.S. application Ser. No. 14/216,790, which is herein incorporated by reference in its entirety. The sharp tipped broach can be advanced over the guide pin and can be tapped directly into the bone to form the curved bore.

The curved implant can then be advanced over the curved guide pin and into the curved insertion path that is formed by the curved pilot bore. In some embodiments, the curved implant can be held by the pivoting arm and inserted into the curved insertion path without the aid of a guide pin by rotating the curved arm.

More generally, the implants described herein can be used to fuse any two bone segments, such as two bones that form a joint or two bones resulting from a fracture.

Implant Rescue

In some cases, an implant will fail to properly fuse with the native bone, which can result in a loose implant and can threaten the stability of the fused bone segments. One solution is to remove the implant and replace it with another implant. The old implant can be removed by chiseling the implant out of bone using a bladed revision tool, such as previously described in co-pending U.S. patent application Ser. No. 14/217,008, which is herein incorporated by reference in its entirety for all purposes.

The implant can then be pulled out of the bone leaving an empty cavity. The cavity is generally of the same shape of the implant, but may be slightly larger due to the bone cutting process. Therefore, the replacement implant that is selected to replace the old implant can be of similar shape but with slightly larger dimensions. For example, an implant that inscribes an 8 mm circle may be suitable as a replacement for an implant that inscribes a 7.5 mm circle. Similarly, a tapered implant such as the tapered implant shown in FIG. 7I can be used. The narrow distal end of the tapered implant can be more easily inserted into the cavity and as the tapered implant is inserted into the cavity, the wider proximal portion can form a secure fit in the cavity.

Alternatively, an implant with a different shape can be inserted into the cavity such that at least one or more portions of the new implant extends into the existing host bone surrounding the cavity. For example, removal of a triangular implant leaves a cavity with a triangular cross-section. Any of the implants illustrated in FIGS. 9A-14B can be inserted into the cavity. For example, any of the implants with ribs can be selected such that the ribs are embedded into the bone surrounding the cavity after insertion into the cavity. In addition, any gaps remaining in the cavity from differences in geometry between the implant and the cavity can be filled with bone graft material and/or a biologic aid. The number of ribs can correspond to the number of sides of the cavity and can be positioned such that each rib is aligned with the center of each side of the cavity.

The implant may be directly tapped into the cavity using a slap hammer or other impact device. In other embodiments, the cavity can be additionally shaped to better receive the implant. For example, a specialized broach with cutouts for the ribs can be used to cut slots into the bone surrounding the cavity, and then the implant can be inserted by aligning the ribs of the implant with the newly cut slots.

The implants can be made of a metal such as titanium, titanium alloy, steel, steel alloy, and the like. Alternatively, the implants can be made of a ceramic, polymer, or bone graft material.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

What is claimed is:

1. A method of implanting a curved implant across a joint or fracture between a first bone segment and a second bone segment, the method comprising:
    forming a curved insertion path from the first bone segment, across the joint or fracture between the first bone segment and the second bone segment, and to the second bone segment, wherein the curved insertion path has a predetermined radius of curvature along its length;
    inserting a curved guidewire along the curved insertion path;
    disposing a drill bit over the curved guidewire;
    drilling a curved bore along the curved guidewire;
    disposing a broach over the curved guidewire;
    shaping the curved bore with the broach to form the insertion path; and
    inserting a curved implant having a matching radius of curvature into the curved insertion path and into the first bone segment, across the joint or fracture, and into the second bone segment.

2. The method of claim 1, wherein the curved guidewire is rotated into the curved insertion path.

3. The method of claim 1, wherein both the shaped insertion path and the curved implant have a transverse overall cross-sectional profile that is rectilinear.

4. The method of claim 1, wherein both the shaped insertion path and the curved implant have a transverse overall cross-sectional profile that is defined by at least one apex.

5. The method of claim 1, wherein both the shaped insertion path and the curved implant have a transverse overall cross-sectional profile that is triangular.

6. The method of claim 1, wherein both the shaped insertion path and the curved implant have a transverse overall cross-sectional profile that is rectangular.

7. The method of claim 1, wherein the curved implant comprises an elongate body with a plurality of fenestrations.

8. The method of claim 7, wherein the fenestrations are located on a distal portion of the elongate body.

* * * * *